United States Patent

Peterman et al.

Patent Number: 5,533,962
Date of Patent: Jul. 9, 1996

[54] RINGLESS ADHESIVE BANDAGE

[76] Inventors: Shadi Peterman; Douglas Peterman, both of 12192 Fox Point Dr., Maryland Heights, Mo. 63043

[21] Appl. No.: 439,852

[22] Filed: May 12, 1995

[51] Int. Cl.⁶ .................................................. A61F 5/00
[52] U.S. Cl. .......................... 602/54; 602/41; 602/43; 602/44; 602/45; 602/57
[58] Field of Search ............................. 602/41–45, 52, 602/54, 57, 58; 128/888–889; 604/304, 305, 307, 308

[56] References Cited

U.S. PATENT DOCUMENTS

| | | | |
|---|---|---|---|
| 2,905,174 | 9/1959 | Smith | 602/42 |
| 3,550,589 | 12/1970 | Wallerstein | 602/42 |
| 3,973,563 | 8/1976 | Green et al. | 602/77 |
| 4,285,338 | 8/1981 | Lemelson | 602/42 |
| 4,334,530 | 6/1982 | Hassell | 602/42 |
| 4,393,150 | 7/1983 | Kresner | 523/111 |
| 4,530,353 | 7/1985 | Lauritzen | 602/42 |
| 4,689,044 | 8/1987 | Murata | 604/306 |
| 4,726,364 | 2/1988 | Wylan | 602/44 |
| 4,743,249 | 5/1988 | Loveland | 604/304 X |
| 4,858,604 | 8/1989 | Konishi | 602/57 |
| 4,899,739 | 2/1990 | Konishi | 604/306 |
| 5,244,523 | 9/1993 | Tollini | 602/900 |
| 5,310,402 | 5/1994 | Rollband | 602/42 |

*Primary Examiner*—Richard J. Apley
*Assistant Examiner*—Kim M. Lee
*Attorney, Agent, or Firm*—Veo Peoples, Jr.; J. William Stader; Peoples & Hale

[57] ABSTRACT

Adhesive bandages having a peripherally-raised non-adhesive thin-layer bordering the adhesive surface of such bandages is disclosed. The non-adhesive thin-layer inhibits formation of dirt rings which would otherwise remain when the adhesive bandage is removed from human skin.

9 Claims, 2 Drawing Sheets

RINGLESS ADHESIVE BANDAGE

BACKGROUND OF THE INVENTION

1. Field of the Invention

The present invention relates to prepared adhesive bandages for first aid and surgical dressings, and particularly to an improved type for preventing dirt rings while wearing the bandages during work or play.

2. Background of the Prior Art

Adhesive bandages of various types are available in strip, piece, or roll form. Each has a bandage main body and an adhesive surface. Most strip and piece bandages, but not all, have a gauze portion disposed at the center of an adhesive surface. Few roll bandages have a gauze portion, but there are some which do. Heretofore, however, all adhesive bandages have comprised an adhesive surface which completely covered the periphery of the bandage main body.

There have been numerous developments, over the years, directed towards particular drawbacks in the design and/or use of one or more types of adhesive bandages. For example, U.S. Pat. No. 3,973,563 discloses a foamed combination of latex and elastomers to provide a more conformable backing. U.S. Pat. No. 4,285,338 discloses a hollow, rigid, plastic shock-absorbing shell outside the central portion to protect the wound. U.S. Pat. No. 4,334,530 discloses directional markings on the bandage to aid in removal without reopening or otherwise damaging the wound covered thereby. U.S. Pat. No. 4,393,150 discloses a fiber reinforced adhesive for maintaining attachment to body surfaces over longer periods of time. U.S. Pat. No. 4,530,353 discloses adhesive-coated areas and adjacent pad areas prepared from a single sheet of heat-fusible bandage material. U.S. Pat. Nos. 4,689,044, 4,858,604 and 4,899,739 disclose special adhesive bandages for holding medicinal agents which impregnate the gauze portion when depressed. U.S. Pat. No. 4,726,364 discloses maintaining the gauze portion in a raised position to prevent deleterious contact between the bandage and the scabs that form on wounds covered thereby. U.S. Pat. No. 5,244,523 discloses replaceable dressings on adhesive bandages.

While such prior art adhesive bandages are effective and desirable, there remains a drawback to the use of strip, piece or roll bandages which heretofore has not been overcome. That is, bandages worn during work or play, which are subjected to dust or dirt, will, upon removal, leave a dark, residual ring of dirt/dust, embedded in, or agglomerated with, adhesive material and located at points along the periphery of the area on which the adhesive surface contacted the body. This dirt ring often necessitates intensively washing the surface of the skin, following removal of the bandage, which can have a deleterious effect on a newly healed wound. Furthermore, the buildup of dirt can be caked to the point that it interferes with freely removing the bandage, which can lead to minor bruises on children at points along the bandage periphery.

SUMMARY OF THE INVENTION

It is therefore an object of the present invention to provide an improved adhesive bandage which inhibits formation of such a dirt ring and the problems which ensue upon removal of adhesive bandages.

It is a further object to avoid disaffecting either the bandage application, adherence, or removal. Other objects, features and advantages of the present invention will become apparent from a further reading of the following summary, description, drawings and claims.

The previously described objectives of the present invention are fulfilled by a peripherally-raised, non-adhesive, thin-layer portion on the upper surface of the bandage main body.

The adhesive bandages of the present invention comprise a bandage main body having an adhesive coating on its upper surface but disposed within a peripherally-raised thin wall of non-adhesive material along the periphery of the bandage main body upper surface. This raised wall consists of a thin-layer of non-adhesive which, depending upon the particular type of bandage desired, may not completely surround the adhesive surface. For example, strip-type bandages most often contain a centrally disposed gauze portion on the adhesive surface, which gauze portion longitudinally extends so close to the periphery of the adhesive portion that absence of adhesive at the periphery would risk deleterious exposure of the wound. Accordingly, the adhesive surface of the present invention may be designed to extend completely to that portion of the periphery closely bordering the gauze, and thereby interrupt an otherwise continuous peripheral wall of thin-layer non-adhesive material. Circular piece-type adhesive bandages can be constructed, if desired, to have a continuous thin-layer at the circumferential periphery of the adhesive surface and therefore also surrounding any centrally disposed gauze portion which may be desired. Butterfly configured adhesive bandages and roll-type bandages, which have no gauze portion at all, may be designed which have the peripherally-raised non-adhesive thin-layer wall either completely or intermittently surrounding the adhesive surface.

DETAILED DESCRIPTION OF THE INVENTION

The bandage main body may comprise any thin sheet of woven or non-woven fabric, plastic material or like capable of receiving and retaining adhesive of the type normally employed for adhesive bandages. These materials, their dimensions, etc., are well known in the industry.

The upper surface of the bandage main body is coated with an adhesive capable of releasably adhering to human skin. Such adhesive are also well known to those skilled in the art.

Generally disposed at the center of the adhesive-coated upper surface of the bandage main body may be a gauze portion. Preferably, the gauze portion is retained in a raised position above said upper surface.

Peel sheets, comprising one or more sections made of, for example, paper, synthetic resin or the like preferably are permanently affixed along the periphery of the bandage main body upper surface, while being releasably or temporarily affixed to the adhesive surfaces at the center inward from the periphery. With such embodiments, the peel sheet is scored or otherwise designed to allow the releasable portion of said peel sheet to be peeled from the bandage main body prior to use of the bandage, so as to leave a non-adhesive peripherally-raised thin-layer on the bandage main body substantially surrounding the adhesive surface.

Alternatively, the peripherally-raised thin-layer on the bandage main body need not be integrally molded from the same peel sheet. It can, if desired, be separately and freely made of the same or different material from the peel sheet. Such separate material is preferably thin plastic material such as cellophane paper or that used to make Saran Wrap®. It has been found that normal customary peel sheet paper can be applied to cover both the thin peripheral layer or wall and the adhesive surface without taking away from the objects of the present invention.

There are numerous advantages to the novel peripheral thin-layer of the present invention but the most important of which is that such a thin-layer surprisingly inhibits the formation of the dirt ring that often surrounds the wound at the periphery of the surface where the adhesive surface contacts the skin. The peripheral thin-layer also facilitates ease of removal of the bandage from the skin and thus serves to inhibit minor pinching and bruising when removing adhesive bandages from the skin.

Figure 1:
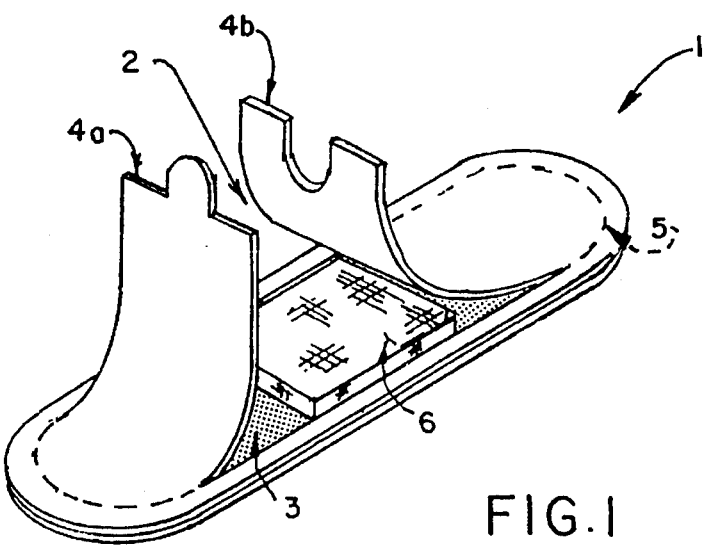
FIG. 1 is a top perspective view of a two peel sheet strip-type bandage preferred embodiment of the present invention.
Figure 2:
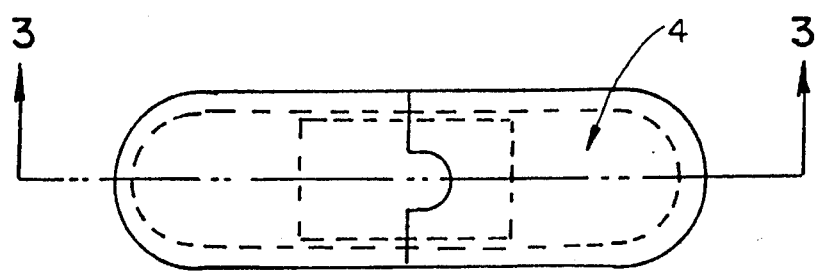
FIG. 2 is a top view of said preferred embodiment.
Figure 3:
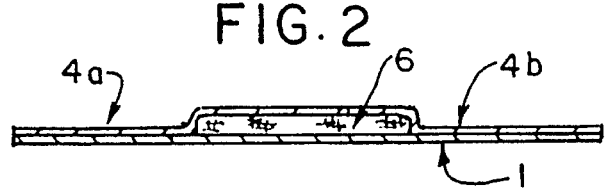
FIG. 3 is a cross-sectional front view through line 3—3 of FIG. 2.

With reference to FIGS. 1, 2 and 3, a preferred embodiment of the present invention will be described. Indicated at 1 is an adhesive bandage main body in the form of a rectangular adhesive sheet which is prepared by applying an adhesive 3 to the upper surface 2 of the adhesive bandage main body. A pad 6 of gauze, absorbent cotton, non-woven fabric or the like, all of which herein commonly referred to as the gauze portion, is affixed to the central portion of the main body i on the upper surface thereof.

A peel sheet, generally indicated at 4 on FIG. 2, comprises sections 4a, 4b and 4c depicted in FIGS. 3 and/or 4. Sections 4a and 4b comprise opposing sections of the center of the general peel sheet 4 which are peelable from section 4c of said peel sheet along score line 5. Score line 5 defines the point of separation from section 4c which is permanently affixed as a peripherally-raised thin-layer which is permanently affixed to the upper surface of the bandage main body 1.

Figure 4:
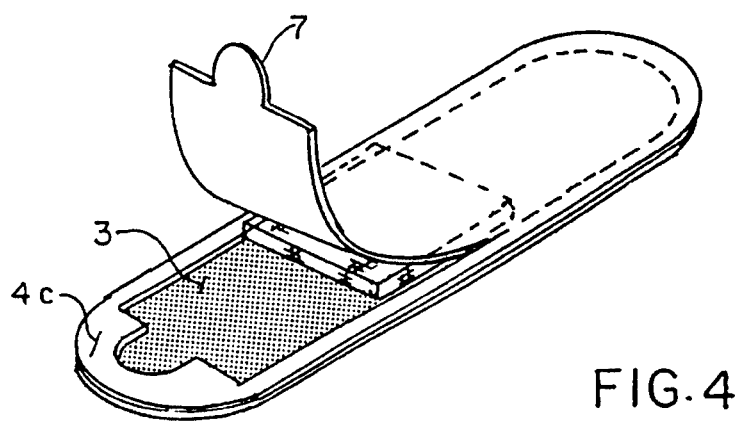
FIG. 4 is a top perspective view of another preferred embodiment strip-type bandage having a single peel sheet.

Referring to FIG. 4, there is indicated at 7 an alternative embodiment of a single peel sheet member which can take the place of, if desired, sections 4a and 4b of the peel sheet shown in FIGS. 1, 2 and 3.

Figure 5:
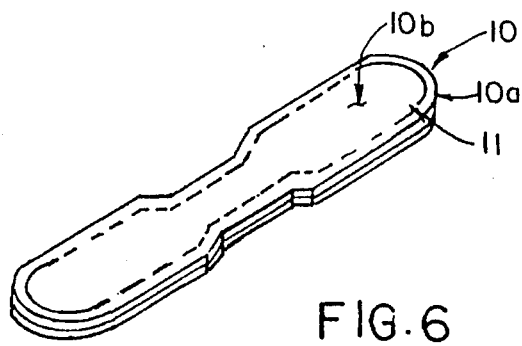
FIG. 5 is a top perspective view of a circular type bandage of the present invention with its peel sheet intact.

Referring to FIG. 5, there is shown a circular adhesive bandage having a peel sheet generally shown at 8, whose center section 8b can be peeled away while leaving peripheral section 8a, when peeled along score line 9.

Figure 6:
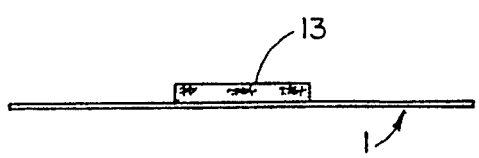
FIG. 6 is a front perspective view of a butterfly-type bandage of the present invention.

FIG. 6 shows a butterfly configured adhesive bandage having a peel sheet 10 which can be peeled along score line 11, while leaving peripheral thin-layer 10a, when removing center peel section 10b.

Figure 7:
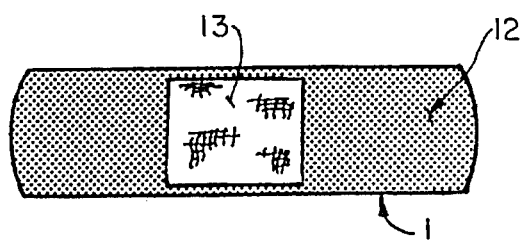
FIG. 7 is a top view of a prior art strip-type bandage.

FIG. 7 shows a strip-type adhesive bandage main body having only adhesive 12 coated over the bandage main body upper surface and having gauze section 13 centrally disposed.

Figure 8:
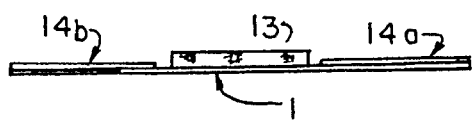
FIG. 8 is a side view of a prior art strip-type bandage.

FIG. 8 is a side view of FIG. 7.

Figure 9:
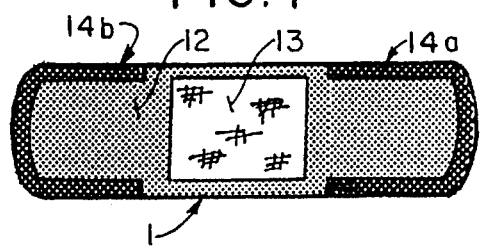
FIG. 9 is a top view of a strip-type bandage of the present invention with an interrupted peripherally-raised non-adhesive thin-layer portion.

FIG. 9 shows an adhesive bandage main body having adhesive 12 coated on its upper surface and showing peripheral sections 14a and 14b comprised of thin cellophane paper, while the periphery is interrupted so as to have adhesive coating extend all the way to the periphery of the adhesive bandage main body upper surface nearest to gauze section 13.

Figure 10:
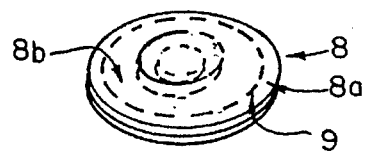
FIG. 10 is a side view of FIG. 9.

FIG. 10 is a side view of FIG. 9.

EXAMPLE 1

Figure 11:
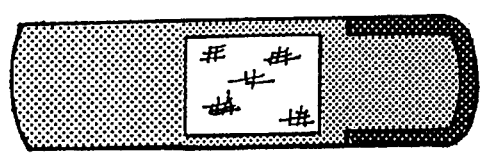
FIG. 11 is a top view of a bandage similar to FIG. 9 but having no 14*b*.
Figure 12:
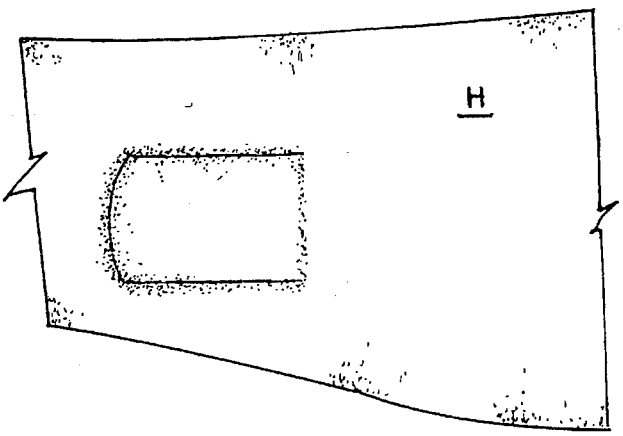
FIG. 12 is an arm showing a dirt ring after removal of the FIG. 11 bandage.

An adhesive bandage such as that illustrated in FIG. 9, except having only the cellophane paper peripheral section 14a without the accompanying section 14b, is depicted in FIG. 11 and applied to the arm H of a child. The bandage is allowed to be worn by the child continuously for a period of three days. Afterwards, the adhesive bandage is removed, and as can be seen from FIG. 12, a dirt ring 15 is formed around that section of the skin where the adhesive coating 12 was allowed to extend entirely to the periphery of the adhesive bandage, not having section 14b. There is no dirt ring associated with that portion of the arm H where section 14a was applied.

What is claimed is:

1. An improved adhesive bandage comprising:
    a bandage main body having an upper surface with a periphery and an inner portion in which
        a. a peripherally-raised, non-adhesive, thin-layer substantially defines the periphery portion of the upper surface; and
        b. an adhesive-coated recessed surface substantially defines the inner portion of the upper surface; said adhesive-coated recessed surface being substantially surrounded by, said peripherally-raised, thin-layer perifery portion;
            said peripherally-raised non-adhesive thin-layer serving to inhibit the formation of a dirt ring which would otherwise remain when the adhesive bandage is removed from human skin.

2. The adhesive bandage of claim 1 further comprising a gauze portion disposed generally at the center of the adhesive-coated recessed inner portion.

3. The adhesive bandage of claim 1 wherein the peripherally-raised thin-layer portion is a first integral part of a peel sheet, said first integral part being permanently affixed along the bandage upper surface's outer periphery, while a second integral part of the peel sheet is detachably adhered to the upper surface's adhesive-coated recessed inner portion, said peel sheet having a score line separating said second part from said first part,
    whereby the peel sheet may be detached along its score line to expose said adhesive-coated inner portion.

4. The adhesive bandage of claim 1 further comprising a non-integral peel sheet, consisting of separate and distinct material from the peripheral thin-layer portion, and said peel sheet being detachably adhered to the adhesive-coated inner portion.

5. The adhesive bandage of claim 1 configured as a strip bandage having a peripheral thin-layer interrupted at the gauze portion to permit the adhesive-coated inner portion to completely surround and seal the gauze portion.

6. The adhesive bandage of claim 2 configured as a circular bandage.

7. The adhesive bandage of claim 2 configured as a strip bandage.

8. The adhesive bandage of claim 1 configured as a roll bandage.

9. The adhesive bandage of claim 2 configured as a roll bandage.

* * * * *